United States Patent
Song et al.

(10) Patent No.: US 11,407,793 B2
(45) Date of Patent: Aug. 9, 2022

(54) **DICARBOXYLIC ACID TRANSPORTER FOR INCREASING OIL YIELD OF *MUCOR CIRCINELLOIDES***

(71) Applicant: SHANDONG UNIVERSITY OF TECHNOLOGY, Zibo (CN)

(72) Inventors: Yuanda Song, Zibo (CN); Junhuan Yang, Zibo (CN); Wu Yang, Zibo (CN); Shaoqi Li, Zibo (CN)

(73) Assignee: SHANDONG UNIVERSITY OF TECHNOLOGY, Shandong (CN)

( * ) Notice: Subject to any disclaimer, the term of this patent is extended or adjusted under 35 U.S.C. 154(b) by 48 days.

(21) Appl. No.: 17/262,960

(22) PCT Filed: Nov. 20, 2019

(86) PCT No.: PCT/CN2019/119644
§ 371 (c)(1),
(2) Date: Jan. 25, 2021

(87) PCT Pub. No.: WO2020/103853
PCT Pub. Date: May 28, 2020

(65) Prior Publication Data
US 2021/0292380 A1 Sep. 23, 2021

(30) Foreign Application Priority Data
Nov. 23, 2018 (CN) .......................... 201811402942.7

(51) Int. Cl.
*C07K 14/37* (2006.01)
*C12N 15/80* (2006.01)

(52) U.S. Cl.
CPC .............. *C07K 14/37* (2013.01); *C12N 15/80* (2013.01); *C12N 2800/10* (2013.01)

(58) Field of Classification Search
None
See application file for complete search history.

(56) References Cited

U.S. PATENT DOCUMENTS

| 8,741,611 B2 | 6/2014 | Brown et al. |
| 8,999,685 B2 | 4/2015 | Brown et al. |
| 2015/0024446 A1 | 1/2015 | Brown et al. |

OTHER PUBLICATIONS

International Search Report dated Feb. 18, 2020 in PCT/CN2019/119644 filed on Nov. 20, 2019, citing documents AA-AC, AO, AP, AX and AY therein, 3 pages.
Li, H.-Q. et al., "Progress of $C_4$-dicarboxylate Transporter in Bacteria," Journal of Hebei University (Natural Science Edition), vol. 27 No. 5, Sep. 2007, pp. 555-560 (with English abstract).
Yang, L. et al., "Overexpression of a $C_4$-dicarboxylate transporter is the key for rerouting citric acid to $C_4$-dicarboxylic acid production in *Aspergillus carbonarius*," Microbial Cell Factories, vol. 16, No. 43, 2017, pp. 1-12.

*Primary Examiner* — Suzanne M Noakes
(74) *Attorney, Agent, or Firm* — SZDC Law P.C.

(57) ABSTRACT

The present application discloses a dicarboxylic acid transporter and its encoding gene dit gene for increasing oil yield of *Mucor circinelloides*, the dit gene is cloned from the high-yield *M. circinelloides* WJ11, and the dit gene is transformed into *M. circinelloides* deficient strain Mu402, the dit gene is integrated into the genome of *M. circinelloides* by homologous recombination to obtain recombinant strain Mc-Dit. The total fatty acid content of the Mc-Dit strain increased by 33.76% and the intracellular lipid content may reach up to 17.67% of the dry biomass.

8 Claims, 1 Drawing Sheet
Specification includes a Sequence Listing.

SEQUENCE LISTING

<160> NUMBER OF SEQ ID NOS: 10

<210> SEQ ID NO 1
<211> LENGTH: 2129
<212> TYPE: DNA
<213> ORGANISM: Mucor circinelloides sp.

<400> SEQUENCE: 1

```
atgccaaaag agccgtctat tgccatttct accgagatac ccaacgaaag cacctgctta      60
ttgcctgtgg acagcactaa cacaacattg gagctgagag aatcaacaaa caaacaaggt     120
```

```
acacatttgt tgttgcgggt aaacatataa acattgcaac ttatgcaact gttgtaggca      180
ttgtagctgc tgttgtgtat cgcaaattca tagcctccaa gctgttcagt ctgctgccat      240
cgcttgccct gggatcagct atttggtttg gcgtgactcc atcagaggaa ctcacattga      300
catccattcg attgctcgca gtgtttacaa ggttcgtctg ggcagccatt gctggtggtt      360
ctgttgcctt atgtgtttta tcttttagt tgtatatttg cactcatcac tacgtcagtt       420
gatatatcag tgctggtctt gactgccctg acactgctgt ccagcacaca ctcatttgtt      480
tgtgaagatc atgttacagg catgagcact gaatgccgtc tctgcggaga gatcaacccc      540
attaccgagg cccctttga atgcaatggt ggtaaggaag cttttcatca ttcgctggag        600
gggttctcaa gctctgttgt gtggttgatt tttgctgctt ttcatctggg aaaagctgtt      660
gaagtaacac agcttggaaa agaaatatca ttattcatga tccgctcatt cggcaagcat      720
gtcataggtt tagcatatgc cattttgctc tcaggtacca ccttaaacac caactaatgt      780
gagagaaacc tgctaataag tttgtatata tatatatata gagttattac tagcccccgt      840
agttcctagc aatacagcgc gaggcggcgg catcgtatta cccgtggtgc attccattgc      900
aactacttta ggttcaacac catctcagaa tcccaagata ggcggatttt tgatgctgat      960
tggcgcacat tccaatctat tgtctgcctc catgtatttg acaggtataa tattcagaat     1020
gtgattgata aaatgaaata ctgacaaggg tcaaataggc atggctccaa atccagtcgt     1080
cttggccaaa gcaaatacac tctaccctga tttgcaattc aatttcatga cctggattac     1140
aggaagctct gttcctgcat tagtcagtgc tgctattttg ccctcctttt tagcatggtc     1200
atgtggcatt tcaaatcaa aggaagaatc cgctcaagtg gaagaaggcc agcaactcaa      1260
ggccagtgga gacgacattg ttcaacacgc ctccaaggaa ttgcatgcaa tggggtccat     1320
gtcaagcaag gaactggtaa gtaaatggtt attaagcatc tagacttcta cttaacaagt     1380
gttattagca actttgctct gttctctgtg tgtgccttgt gatgtgggta acgtccggct     1440
acactaaaat agattcaacc ttggttgctt taatcggcat tgtagcctta ttacatatgg     1500
acactaaaat agattcaacc ttggttgctt taatcggcat tgtagcctta ttacatatgg     1560
caaaagtatg ccaaattagc acttacactt acccacacac actctctttt tatctcttat     1620
agtgggaaac attgttttgg ttgggcgggt ttgtaacgat tgccactcaa ctctctgaag     1680
caggagcatc tggctatatt ggccataaag tgtctttggc tattacgcac ctcaaattgc     1740
ccgctgtgcc tgccttggct attgcttatt tccttacgac attcatgttc tcttccctga     1800
gcgctcatac cgtggcattt gtagctacct ttttggatgc agggcattca ttaggtgcca     1860
acccaatgat actgacttgc ttgctcgctt attttggagc tcttggtggt tgcatggtat     1920
gatgtcgatt cgcgcagagt gcaacttaat aagcgactaa tttgaataca tagacaaact     1980
tttctacagg aagcttggcc atgtattatg ctccaggtta tgtttctcgt tcgaaatggt     2040
ttgtcgttgg tggacagata gcattgctct acctcgtcat ctactttact tttggtatgg     2100
gctggtggaa actttgggc tggtgttga                                        2129
```

<210> SEQ ID NO 2
<211> LENGTH: 566
<212> TYPE: PRT
<213> ORGANISM: Mucor circinelloides sp.

<400> SEQUENCE: 2

Met Pro Lys Glu Pro Ser Ile Ala Ile Ser Thr Glu Ile Pro Asn Glu
1               5                   10                  15

-continued

```
Ser Thr Cys Leu Leu Pro Val Asp Ser Thr Asn Thr Thr Leu Glu Leu
             20                  25                  30

Arg Glu Ser Thr Asn Lys Gln Gly Ile Val Ala Val Val Tyr Arg
         35                  40                  45

Lys Phe Ile Ala Ser Lys Leu Phe Ser Leu Leu Pro Ser Leu Ala Leu
 50                  55                  60

Gly Ser Ala Ile Trp Phe Gly Val Thr Pro Ser Glu Glu Leu Thr Leu
 65                  70                  75                  80

Thr Ser Ile Arg Leu Leu Ala Val Phe Thr Ser Cys Ile Phe Ala Leu
             85                  90                  95

Ile Thr Thr Ser Val Asp Ile Ser Val Leu Val Leu Thr Ala Leu Thr
             100                 105                 110

Leu Leu Ser Ser Thr His Ser Phe Val Cys Glu Asp His Val Thr Gly
             115                 120                 125

Met Ser Thr Glu Cys Arg Leu Cys Gly Glu Ile Asn Pro Ile Thr Glu
 130                 135                 140

Ala Pro Phe Glu Cys Asn Gly Lys Glu Ala Phe His His Ser Leu
145                 150                 155                 160

Glu Gly Phe Ser Ser Ser Val Val Trp Leu Ile Phe Ala Ala Phe His
             165                 170                 175

Leu Gly Lys Ala Val Glu Val Thr Gln Leu Gly Lys Arg Ile Ser Leu
             180                 185                 190

Phe Met Ile Arg Ser Phe Gly Lys His Val Ile Gly Leu Ala Tyr Ala
             195                 200                 205

Ile Leu Leu Ser Glu Leu Leu Leu Ala Pro Val Val Pro Ser Asn Thr
 210                 215                 220

Ala Arg Gly Gly Gly Ile Val Leu Pro Val Val His Ser Ile Ala Thr
225                 230                 235                 240

Thr Leu Gly Ser Thr Pro Ser Gln Asn Pro Lys Ile Gly Gly Phe Leu
             245                 250                 255

Met Leu Ile Gly Ala His Ser Asn Leu Leu Ser Ala Ser Met Tyr Leu
             260                 265                 270

Thr Gly Met Ala Pro Asn Pro Val Val Leu Ala Lys Ala Asn Thr Leu
             275                 280                 285

Tyr Pro Asp Leu Gln Phe Asn Phe Met Thr Trp Ile Thr Gly Ser Ser
 290                 295                 300

Val Pro Ala Leu Val Ser Ala Ala Ile Leu Pro Leu Leu Leu Ala Trp
305                 310                 315                 320

Ser Cys Gly Ile Phe Lys Ser Lys Glu Glu Ser Ala Gln Val Glu Glu
             325                 330                 335

Gly Gln Gln Leu Lys Ala Ser Gly Asp Asp Ile Val Gln His Ala Ser
             340                 345                 350

Lys Glu Leu His Ala Met Gly Ser Met Ser Lys Glu Leu Gln Leu
             355                 360                 365

Cys Ser Val Leu Cys Val Cys Leu Val Met Trp Val Thr Ser Gly Tyr
 370                 375                 380

Thr Lys Ile Asp Ser Thr Leu Val Ala Leu Ile Gly Ile Val Ala Leu
385                 390                 395                 400

Leu His Met Gly Thr Ile Arg Trp Lys Asp Val Ala Asn Asn Thr Asn
             405                 410                 415

Ala Trp Glu Thr Leu Phe Trp Leu Gly Gly Phe Val Thr Ile Ala Thr
             420                 425                 430

Gln Leu Ser Glu Ala Gly Ala Ser Gly Tyr Ile Gly His Lys Val Ser
```

```
                        435                 440                 445
Leu Ala Ile Thr His Leu Lys Leu Pro Ala Val Pro Ala Leu Ala Ile
            450                 455                 460
Ala Tyr Phe Leu Thr Thr Phe Met Phe Ser Ser Leu Ser Ala His Thr
465                 470                 475                 480
Val Ala Phe Val Ala Thr Phe Leu Asp Ala Gly His Ser Leu Gly Ala
                485                 490                 495
Asn Pro Met Ile Leu Thr Cys Leu Leu Ala Tyr Phe Gly Ala Leu Gly
            500                 505                 510
Gly Cys Met Thr Asn Phe Ser Thr Gly Ser Leu Ala Met Tyr Tyr Ala
        515                 520                 525
Pro Gly Tyr Val Ser Arg Ser Lys Trp Phe Val Val Gly Gly Gln Ile
            530                 535                 540
Ala Leu Leu Tyr Leu Val Ile Tyr Phe Thr Phe Gly Met Gly Trp Trp
545                 550                 555                 560
Lys Leu Leu Gly Trp Cys
                565

<210> SEQ ID NO 3
<211> LENGTH: 51
<212> TYPE: DNA
<213> ORGANISM: Artificial Sequence
<220> FEATURE:
<223> OTHER INFORMATION: Mudit-F

<400> SEQUENCE: 3 actttatat acaaaataac taaatctcga gatgccaaaa gagccgtcta t            51

<210> SEQ ID NO 4
<211> LENGTH: 46
<212> TYPE: DNA
<213> ORGANISM: Artificial Sequence
<220> FEATURE:
<223> OTHER INFORMATION: Mudit-R

<400> SEQUENCE: 4
actagtcgca attgccgcgg ctcgagtcaa caccagccca aaagtt                 46

<210> SEQ ID NO 5
<211> LENGTH: 29
<212> TYPE: DNA
<213> ORGANISM: Artificial Sequence
<220> FEATURE:
<223> OTHER INFORMATION: 1552-F

<400> SEQUENCE: 5
cctcggcgtc atgatgtttt tgtgtacct                                    29

<210> SEQ ID NO 6
<211> LENGTH: 27
<212> TYPE: DNA
<213> ORGANISM: Artificial Sequence
<220> FEATURE:
<223> OTHER INFORMATION: 1552-R

<400> SEQUENCE: 6
gggatgtctg ctgctaccat gtctcat                                      27

<210> SEQ ID NO 7
<211> LENGTH: 29
<212> TYPE: DNA
<213> ORGANISM: Artificial Sequence
```

```
<220> FEATURE:
<223> OTHER INFORMATION: WJ11-dit-F

<400> SEQUENCE: 7
ccataaagtg tctttggcta ttacgcacc                                              29

<210> SEQ ID NO 8
<211> LENGTH: 25
<212> TYPE: DNA
<213> ORGANISM: Artificial Sequence
<220> FEATURE:
<223> OTHER INFORMATION: WJ11-dit-R

<400> SEQUENCE: 8
accaagagct ccaaaataag cgagc                                                  25

<210> SEQ ID NO 9
<211> LENGTH: 19
<212> TYPE: DNA
<213> ORGANISM: Artificial Sequence
<220> FEATURE:
<223> OTHER INFORMATION: actin-F

<400> SEQUENCE: 9
gatgaagccc aatccaaga                                                         19

<210> SEQ ID NO 10
<211> LENGTH: 19
<212> TYPE: DNA
<213> ORGANISM: Artificial Sequence
<220> FEATURE:
<223> OTHER INFORMATION: actin-R

<400> SEQUENCE: 10
ttctcacggt tggacttgg                                                         19
```

DICARBOXYLIC ACID TRANSPORTER FOR INCREASING OIL YIELD OF *MUCOR CIRCINELLOIDES*

SEQUENCE LISTING

The instant application contains a Sequence Listing which has been submitted electronically in ASCII format and is hereby incorporated by reference in its entirety. Said ASCII copy, created on Jun. 4, 2021, is named 533498USSL.txt and is 9,603 bytes in size.

CROSS REFERENCE TO RELATED APPLICATION

This application is a 371 national stage application of International Application PCT/CN2019/119644, filed on Nov. 20, 2019, which claims the priority of Chinese Patent Application No. 201811402942.7 entitled "Dicarboxylic acid transporter for increasing oil yield of *Mucor circinelloides*" filed with China National Intellectual Property Administration on Nov. 23, 2018, the contents of which are which is incorporated herein by reference in their entirety.

TECHNICAL FIELD

The present application belongs to the technical field of genetic engineering, especially relating to a dicarboxylic acid transporter for increasing oil yield of *Mucor circinelloides*.

BACKGROUND ART

These days, people's living standard is progressively improved, and more individuals pay attention to the health and the quality of life. The important active polyunsaturated fatty acids in the oil, such as γ-linolenic acid (GLA), α-linolenic acid (ALA), lithospermic acid (stearidonic acid, SDA), eicosapentaenoic acid (EPA) and docosahexaenoic acid (DHA) are thenutritional components of our dietary oil that maintain lipid metabolism in our body and prevent the occurrence of various chronic diseases. γ-linolenic acid is an essential fatty acid for the human body which acts as precursor substance to synthesize other active polyunsaturated fatty acids. At present, most of the industrial γ-linolenic acid comes from plants, such as evening primrose, borage oil, and blackcurrant seed oil. However, due to the influence of producing area and climate, the growth cycle of plants is short and the yield is unstable, which can not meet the market demand. Therefore, searching for novel oil resources has become a hot research topic. The oleaginous microorganisms have attracted much attention due to the characteristics of high oil content, short growth cycle, wide spectrum utilization of carbon source. The oleaginous microbial cell factories refer to the use of oleaginous microorganisms in the fermentation process, in which excessive carbon sources, such as carbohydrates, hydrocarbons, etc. are added so that the intracellular fatty acids of the microorganisms are stored in their bodies in the form of triglycerides, and then the cells are turned into cell factories. Therefore, using microbial oil and its derivatives to replace some plant resources may play an important role in the future biological oil production industry.

*M. circinelloides* is the world's first commercial cultured strain for producing oils and fats. *Mucor circinelloides* is used as a model strain for researching oleaginous microorganisms. However, a new *M. circinelloides* strain WJ11 was isolated in this study, which produces lipids that may account for 36% of the dry cell weight, its genome sequencing is completed, and the research on the genetic background and the oil production mechanism is studied in detail, and meanwhile, genetic manipulation is under process thereof is simple, various genetic tools are available, so that to make it is more suitable for preparation of oil cell factories. *M. circinelloides* may produce a large amount of γ-linolenic acid (GLA), which has important physiological functions in the human body, and this is its main commercial value.

The dicarboxylic acid transporter (2-oxoglutarate/malate transporter, dit) gene is one of the key factors in lipid synthesis. Under the condition of sufficient carbon source and lack of other nutrients (such as nitrogen, phosphorus, sulfur, etc.), which almost shuts down the tricarboxylic acid cycle of oleaginous fungi, resulting a large amount of citric acid accumulation in mitochondria. At this time, citric acid is transported to the cytoplasm and is cleaved by a citrate acid lyase to produce acetyl coenzyme A and oxaloacetate. Acetyl coenzyme A is a precursor substance for synthesizing oil and fat in cells, which is then used to synthesize fatty acids through biochemical reactions, and fatty acids are stored in cells in the form of triglycerides to form microbial oil. It has been reported that a dicarboxylic acid transporter can transport malic acid and other dicarboxylic acids from the cytoplasm into mitochondria through the mitochondrial membrane, thereby promoting the transport of citric acid and the synthesis of cellular oils and fats. Therefore the dicarboxylic acid transporter plays an important role in the synthesis and accumulation of microbial oils and fats.

SUMMARY OF THE INVENTION

The purpose of the present application is to provide a dicarboxylic acid transporter for increasing the oil yield of *M. circinelloides*, so as to increase the oil yield of the *Mucor circinelloides*.

In order to achieve the above object, the present application provides the following schemes:

The present application provides a dicarboxylic acid transporter for increasing the oil yield of *M. circinelloides*, the amino acid sequence of the dicarboxylic acid transporter is set forth in SEQ ID NO:2.

The application also provides a dit gene for coding the dicarboxylic acid transporter, and the nucleotide sequence of the dit gene is set forth in SEQ ID NO. 1.

The application also provides a recombinant vector containing the dit gene.

In some embodiments, the recombinant vector can express the dicarboxylic acid transporter of *M. circinelloides*, and the vector is an expression vector of *M. circinelloides*.

In some embodiments, pMAT1552 is an original vector to obtain target gene recombinant vector.

The application also provides a transformant containing the recombinant vector in the above scheme.

In some embodiments, the transformant with recombinant vector can express the dicarboxylic acid transporter of *M. circinelloides*.

In some embodiments, *M. circinelloides* is a host strain of the recombinant vector.

In some embodiments, the *M. circinelloides* strain includes *M. circinelloides* deficient strain Mu402.

The present application also provides a use of the dicarboxylic acid transporter or the dit gene or the recombinant vector or the recombinant *M. circinelloides* for increasing the oil yield.

The technical scheme of the application is as follows: extracting mRNA of *M. circinelloides* WJ11 strain to be reverse transcribed to cDNA, designing specific primers to amplify dicarboxylic acid transporter (dit) gene by PCR and linking the gene to integrative plasmid pMAT1552, then electrically transforming the recombinant plasmid into protoplast of *M. circinelloides* deficient strain Mu402, selecting positive clones for fermentation culture, wherein the fermentation conditions are as follows: using Kendrick culture medium, 28° C., 700 rpm, air intake 1 v/vmin$^{-1}$, pH 6.0. During the fermentation process, collecting samples according to oil accumulation law and determining the oil content and composition.

The beneficial effects of the present application: the present application provides a dicarboxylic acid transporter for increasing the oil yield of *M. circinelloides*, and the recombinant transformant strain Mc-Dit constructed by using the gene encoding the dicarboxylic acid transporter. Compared with the control strain Mc1552, the yield of the intracellular lipid produced by the recombinant strain Mc-Dit is increased by 33.76%, and the content of the intracellular lipid can reach to 17.67% of the dry biomass. The present application uses *M. circinelloides* as a model strain for studying oil producing cell factories, by utilizing the genetic engineering method. The present application also provides direction for popularizing the industrial application of the *M. circinelloides*, that produces polyunsaturated fatty acids with high nutritional value which meets the growing requirements of health and high-quality life.

DETAILED DESCRIPTION OF THE EMBODIMENTS

Figure 1:
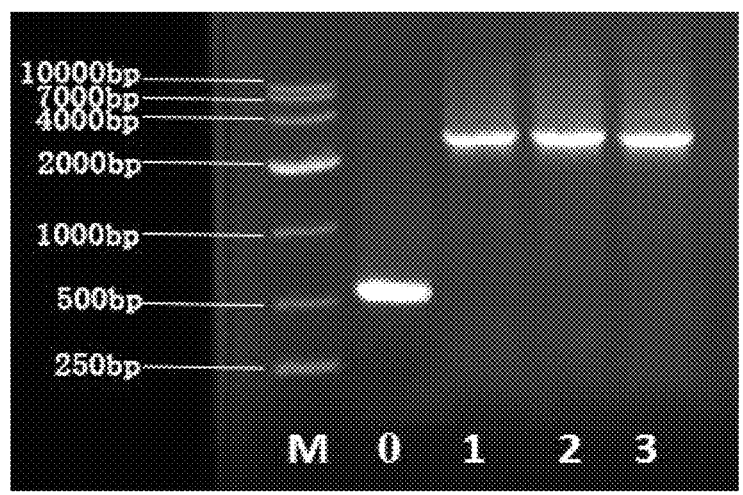
FIG. 1 is a PCR spectrum for identification of recombinant strain of *Mucor circinelloides*, where M represents standard nucleic acid molecular weight; 0 represents a control strain Mc1552; 1-3 represents recombinant strain Mc-Dit of *Mucor circinelloides*.

The present application will be further described below with reference to examples.

EXAMPLE 1

Informatics Analysis of Dicarboxylic Acid Transporter (dit) Gene

According to the genome information of the sequenced WJ11, a dicarboxylic acid transporter (dit) gene (000 239.15, 2129 bp) (the nucleotide sequence of which was set forth in SEQ ID NO: 1) was found, and the gene sequence was used for informatics analysis. The coding region of this sequence was a 1701 bp base sequence, which could code 566 amino acids (the sequence of the amino acids as set forth in SEQ ID NO: 2), and the predicted molecular weight was 60.62 kDa and PI was 6.56, and the protein coded by the sequence had homology of 67% and 75% respectively with a dicarboxylic acid transporter (dit) gene (NCBI gene ID: GAN03794.1) from *Mucor ambiguuss* and a malic acid transporter YflS gene (NCBI gene ID: OBZ90888.1) from *Choanephor cucurbitarum*, so that it is preliminarily determined that the gene could code the dicarboxylic acid transporter of *M. circinelloides* WJ11.

EXAMPLE 2

Construction of Recombinant Plasmid

The *M. circinelloides* WJ11 strain was inoculated into a 500 mL baffled flask which contained 100 mL of Kendrick medium (glucose 30 g/L, MgSO$_4$.7H$_2$O 1.5 g/L, ammonium tartrate 3.3 g/L, KH$_2$PO$_4$ 7.0 g/L, Na$_2$HPO$_4$ 2.0 g/L, yeast extract 1.5 g/L, CaCl$_2$ 0.076 g/L, FeCl$_3$.6H$_2$O 8 mg/L, ZnSO$_4$.7H$_2$O 1 mg/L, CuSO$_4$.5H$_2$O 0.1 mg/L, Co(NO$_3$)$_2$.6H$_2$O 0.1 mg lL, MnSO$_4$.5H$_2$O 0.1 mg/L), cultured at 28° C., 150 rpm, for 24 h. The samples were collected by suction filtration, and DNA was extracted. According to the genome information of sequenced WJ11, the dicarboxylic acid transporter (dit) gene (scaffold00239.15, 2129 bp) was found (the nucleotide sequence was wet forth in SEQ ID NO:1), and the specific primer Mudit-F and Mudit-R were designed according to the gene sequence, the *M. circinelloides* cDNA was used as template for PCR amplification, Mudit-F: 5'-AC TTTTATATA-CAAAATAACTAAATCTCGAGATGC-CAAAAGAGCCGTCTAT-3' (set forth in SEQ ID NO:3), Mudit-R: 5'-ACTAGTCGCAATTGCCGCGGCTCGAGT-CAACACCAGCCCAAAAGTT-3' (set forth in SEQ ID NO: 4).

The PCR reaction was conducted according to the PrimeSTAR HS DNA Polymerase (Takara) instruction. The reaction conditions were as follows: denaturing at 95° C. for 3 min, followed by cycles of denaturing at 95° C. for 30 seconds, annealing at 55° C. for 30 seconds, and extending at 72° C. for 1 min. After a total of 30 cycles, extending at 72° C. for 10 minutes, then cooling to 4° C. for 5 minutes. 2129 bp of amplified PCR fragment was obtained and purified. The purified fragment was inserted into the Xhoi I endonuclease treated vector pMAT1552, using one-step cloning technology. The ligation product was mixed with *Escherichia coli* Top10 competent cells and then the mixture was transformed by heat shock. the transformed product was added into 1 ml of LB liquid medium (peptone 10 g/L, yeast extract 5 g/L, NaCl 10 g/L), incubated at 37° C. for 1 h and then coated on LB medium plate containing 100 mg/L ampicillin (peptone 10 g/L, yeast extract 5 g/L, NaCl 10 g/L, agar 1.5%). After cultured at 37° C. overnight, the colonies were selected and inoculated into LB liquid medium. The plasmids were extracted and sequenced after 8-10 hours, the plasmids with correct sequence were named pMAT1552-Dit.

EXAMPLE 3

Preparation of *M. circinelloides* Protoplasts

The spores of *M. circinelloides* Mu402 strain were inoculated onto plates of YPG medium (yeast extract 3 g/L, peptone 10 g/L, glucose 20 g/L, leucine 20 µg/mL, uracil 200 µg/mL, pH 4.5), and cultured at 28° C. for 1 day. The monoclonal hyphae were spot inoculated onto the plates of YPG medium, and cultivated at 28° C. for 3-4 days to obtain the well-grown spores. The plates with well-grown spores were taken, 5-6 mL of YPG medium was added to each plate, the spores were scraped with a sterilized coating rod, the spore suspension was collected into a sterilized 50 mL centrifuge tube, the concentration of the spores in the suspension was calculated by using a blood cell counting plate, and the concentration of spores was adjusted to 1×10⁷/ml by using YPG with pH 4.5. 12.5 mL of the above spore suspension was taken into a sterilized 250 mL conical flask and placed in a refrigerator at 4° C. overnight to make the spores fully absorb water and expand. The conical flask was kept on a shaker at 30° C. and 250 rpm until the spores germinated. The spores were washed twice by using 5 mL of PS buffer with pH 6.5 (18.22 g of sorbitol and 20 mL, of PBS buffer (NaCl 137 mM, KCl 2.7 mM, $Na_2HPO_4$ 10 mM, $KH_2PO_4$ 2 mM))after centrifugation at 1100 rpm, and the medium was washed away. The cells were resuspended in 5 ml of PS buffer, the lyase at a final concentration of 4 mg/ml and a chitosanase at 0.06 U/ml was added, and incubated for 90 min in a shaker at 30° C. and 60 rpm to remove cell walls. The products after incubation were centrifugated at 100×g, and then washed twice with 0.5 M sorbitol pre-cooled at 4° C., 800 μL of 0.5 M sorbitol was added and gently blew and suctioned to resuspend the precipitate to obtain protoplasts, and the protoplasts were sub packaged in 100 μL/tubes for use.

EXAMPLE 4

Construction of Recombinant Strain Mc-Dit

100 μL of the prepared protoplasts were taken to mix with 1 μg of plasmid pMAT1552-Dit or pMAT1552, and the mixture was transformed by electro transformation. 1 mL of pre-chilled YPGS (sorbitol 0.5 mol/L, yeast extract 3 g/L, peptone 10 g/L, glucose 20 g/L) was added immediately after the electric shock, incubated at 26° C. and 100 rpm for 1 h, YPGS was removed by centrifugation at 100×g, the precipitate was resuspended by using YNBS (sorbitol 91.1 g/L, glutamic acid 1.5 g/L, $(NH_4)_2SO_4$ 1.5 g/L, Yeast Nitrogen Base 0.5 g/L, glucose 10 g/L, adjusted pH to 4.5, thiamine and nicotinic acid were added to a final concentration of 1 μg/mL after sterilization), and then uniformly coated on the MMC selective medium (Casamino acid 10 g/L, Yeast Nitrogen Base 0.5 g/L, glucose 20 g/L, agar 15 g/L, adjusted to pH 3.2, thiamine and nicotinic acid were added to a final concentration of 1 μg/mL after sterilization), cultured avoid light at 28° C. for 3~4 days. Eight single colonies of hyphae growing on the selective plates were randomly picked up and transferred to a new MMC plate, cultured at 28° C. for 2~3 days to collect spores, and about 200 to 300 spores were respectively inoculated on MMC plates and MMC plates containing uracil, cultured at 28° C. for 2~3 days to perform colony count, repeated the above screening steps until the growing number of the spores on the two plates was the same, indicating that stable genetic transformants were obtained. The stable genetic transformants hyphae were cultured on YPG medium plated at 30° C. for 5-7 days, and then spores were collected, the spore concentration was adjusted to 1×10⁷ cells/mL, and the spores were stored in 30% glycerol tube at −80° C. Finally, the recombinant strain Mc-Dit of *M. circinelloides* and the control strain Mc1552 were obtained. The remaining fungal cells cultured in the shake flask after coating were separated by vacuum filtration with a Buchner funnel, and the genomic DNA of *M. circinelloides* was extracted (by referring to the instructions of the plant rapid DNA extraction kit), the genomic DNA was used as a template and 1552-F and 1552-R were used as the primer (the pair of primers were respectively at a position 600 bp upstream and downstream of the inserted target gene site locus in the plasmid) for PCR identification.

```
1552-F:
                       (set forth in SEQ ID NO: 5)
5'-CCTCGGCGTCATGATGTTTTTGTGTACCT-3', 1552-R:
                       (set forth in SEQ ID NO: 6)
5'-GGGATGTCTGCTGCTACCATGTCTCAT-3'.
```

The reaction system and amplification conditions were as follows: denaturing at 95° C. for 3 min, denaturing at 95° C. for 30 seconds, annealing at 60° C. for 30 seconds, and extending at 72° C. for 2 min, 30 cycles, and final extending at 72° C. for 10 minutes. The PCR identification result was as shown in FIG. 1. The fragment obtained by the recombinant strain Mc-Dit of *M. circinelloides* is 2301 bp, while the fragment obtained by the corresponding position of the control strain Mc1552 is 600 bp, indicating that the plasmid has been successfully transformed into *M. circinelloides*.

EXAMPLE 5

Determination of the Expression Level of Dicarboxylic Acid Transporter Gene (dit)

The mRNA of 3, 24, 48, 27 h fermented samples was extracted according to the Trizol instruction manual, and the mRNA was reversed to cDNA by using the ReverTra Ace qPCRRT Kit (Roche), the expression level of the dicarboxylic acid transporter was determined by using the RT-qPCR method, the data were processed by using the $2^{-\Delta\Delta Ct}$ method, SYBR Green Realtime PCR Master Mix (Roche) was used as the kit in the determination process, and the amplification primer sequences were as follows:

```
WJ11-dit-F
                       (set forth in SEQ ID NO: 7)
5'-CCATAAAGTGTCTTTGGCTATTACGCACC-3', WJ11-dit-R
                       (set forth in SEQ ID NO: 8)
5'-ACCAAGAGCTCCAAAATAAGCGAGC-3',
```

Actin was the reference gene, and the amplification primer sequences were as follows:

```
actin-F
                       (set forth in SEQ ID NO: 9)
5'-GATGAAGCCCAATCCAAGA-3', actin-R
                       (set forth in SEQ ID NO: 10)
5'-TTCTCACGGTTGGACTTGG-3'.
```

Figure 2:
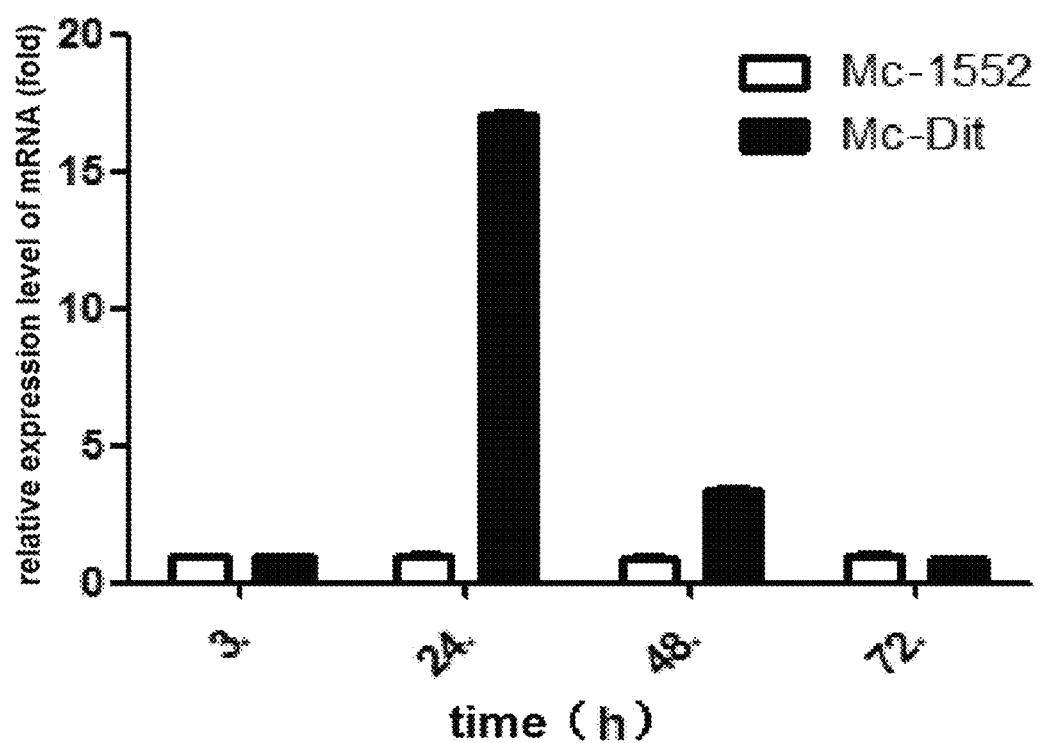
FIG. 2 is a graph showing the determination of the mRNA expression level of the dit gene of the recombinant strain of *Mucor circinelloides*.

The amplification conditions were as follows: preheating at 95° C. for 10 min, then 95° C. for 30 s, 59° C. for 10 s, and 72° C. for 30 s (45 cycles). The result of dit gene expression was as shown in FIG. 2. In Mc-Dit, the dit gene was successfully expressed, and the gene expression level was decreased after 24 hours, but the gene expression level was still at a higher level compared with the control.

EXAMPLE 6

Fatty Acid Composition and Content Determination of Recombinant Strain Mc-Dit of *M. circinelloides*

Preparation of samples to be tested: the recombinant strain Mc-Dit of *M. circinelloides* was cultured on Kendrick medium in a 2 L fermentor. The fermentation conditions were 28° C., 700 rpm, air intake 1 v/v min$^{-1}$, and pH maintained at 6.0. The whole fermentation broth sample was collected according to the oil production law of *M. circinelloides*, and vacuum filtrated with a Buchner funnel, the fermentation broth and the mycelium were separated, the fermentation broth was collected and stored at −20° C. to reserve, the mycelium were washed for 3 times with distilled water, then lyophilized to reserve.

The oil in dry microbial cells of recombinant strain Mc-Dit was extracted with an organic solvent, using a wall breaking method which combining acid treatment and repeated freezing and thawing, the method was appropriately modified according to (Folch J, Lees M, Sloane-Stanley G, et al. A simple method for the isolation and purification of total lipids from animal tissues. BiolChem, 1957,226,497-509), the specific method was as follows:

1) After grinding the freeze-dried cells, 20 mg dry weight of cells was weighed into a 5 mL glass bottle, and 2 mL of 4 M hydrochloric acid was add;

2) The mixture was placed in a water bath at 80° C. for 1 h, at −80° C. for 15 min, repeated once;

3) After returning to room temperature, 1 mL of methanol and 1 mL of chloroform were added, and 100 μL of internal standard C15:0 with a concentration of 2.02 μg/μL was added by using a micro-injector;

4) The mixed solution obtained above was put in a whirlpool mixer for rotation extraction for 0.5 h, centrifuged at 3000 rpm for 3 min, and the chloroform layer was collected in a new 5 mL glass bottle;

5) 1 mL of chloroform was added to the original glass bottle again, repeated the process of 4) and the chloroform layers were combined;

6) The combined chloroform layer solution was blow-dried with nitrogen;

7) 1 mL of 10% methanol solution of hydrochloric acid was added, the added mixed solution was placed in a water bath at 60° C. for 3 hours, and oscillated for 30 seconds every half an hour during the period;

8) 2 mL of n-hexane and 1 mL of saturated NaCl solution were added after cooling to room temperature, the above solution was mixed evenly by vortex and oscillation, and centrifuged at 4000 rpm for 3 min. 1 mL of n-hexane layer was aspirated and transferred to a gas-phase bottle to obtain a fatty acid methyl ester solution.

Commercial fatty acid methyl ester standards (mixed standard of 37 kinds of fatty acid methyl esters) was used as a standard sample to analyze the fatty acid methyl ester by gas chromatography. The gas chromatograph was Agilent GC-6890N in America, the measurement conditions were as follows: gas chromatographic conditions: Splitless injecting samples, the chromatographic column was DM-FFAP (30 m×0.32 min, 0.22 μm), a flame ionization detector, nitrogen was carrier gas, the temperature of a gasification chamber and the temperature of the detector were both 250° C., and the injection volume was 1 μL. Temperature rising procedure: the initial temperature was 80° C., firstly, the temperature was raised to 200° C. at a heating rate of 8° C./min, then the temperature was raised to 205° C. at a heating rate of 1° C./min, and finally the temperature was raised to 240° C. at a heating rate of 4° C./min, kept for 5 min. Pentadecanoic acid (C15:0) was taken as a reference, the peak area of each fatty acid composition was recorded, and the total fatty acid content was calculated. The results were shown in Table 1. The fatty acid composition of the intracellular of the over-expression strain Mc-Dit had little change, but the total fatty acid content of the over-expression strain Mc-Dit was increased by 33.76%, and the intracellular lipid content could reach un to 17.67% of the total fatty acid.

TABLE 1

Oil content of control strain and dit over-expression strain by fermentation culture

| | | Fermentation time (h) | | | | | | | |
|---|---|---|---|---|---|---|---|---|---|
| | | 12 | 24 | 36 | 48 | 60 | 72 | 84 | 96 |
| strain | Mc-Dit | 8.12 | 13.16 | 16.52 | 17.67 | 17.02 | 17.32 | 17.19 | 17.37 |
| | Mc1552 | 5.90 | 9.31 | 11.86 | 12.39 | 12.40 | 12.86 | 13.21 | 13.04 |

From this, it can be determined that the protein encoded by the 000 239.15 gene of *M. circinelloides* WJ11 is a dicarboxylic acid transporter, and the protein is successfully expressed in the recombinant strain Mc-Dit, the protein participates in the oil synthesis process of *M. circinelloides*, and the intracellular oil production of the strain may effectively increase by over-expressing the transporter.

The above description of the embodiments is only used to help understand the method and core idea of the present application. it should be understood by those skilled in the art that, without departing from the principle of the present application, several improvements and modifications can be made, and these improvements and modifications also should be regarded as the protection scope of the present application fall into the scope of the present application. Various modifications to these embodiments will be obvious to those skilled in the art, and the general principles defined herein may be implemented in other embodiments without departing from the spirit or scope of the present application. Therefore, the present application will not be limited to the embodiments shown in this document, but should conform to the widest scope consistent with the principles and novel features disclosed herein.

What is claimed is:

1. A recombinant vector comprising a dit gene encoding a dicarboxylic acid transporter for increasing oil yield of *Mucor circinelloides*, wherein the dicarboxylic acid transporter comprises the amino acid sequence of SEQ ID NO:2, and wherein the dit gene is inserted into a base vector pMAT1552, and wherein the dit gene comprises the nucleotide sequence of SEQ ID NO:1.

2. The recombinant vector according to claim 1, wherein the recombinant vector is capable of expressing the dicarboxylic acid transporter of *M. circinelloides*.

3. A transformant comprising the recombinant vector of claim 1.

4. The transformant according to claim 3, wherein the transformant comprising the recombinant vector is capable of expressing the dicarboxylic acid transporter of *M. circinelloides*.

5. The transformant according to claim 3, wherein *M. circinelloides* is a host strain of the recombinant vector bacterium.

6. The transformant according to claim 5, wherein the *M. circinelloides* is *M. circinelloides* deficient strain Mu402.

7. The recombinant vector according to claim 1, wherein the recombinant vector is for gene expression in *M. circinelloides*.

8. The transformant according to claim 3, wherein the recombinant vector is for gene expression in *M. circinelloides*.

* * * * *